United States Patent [19]

Delbende et al.

[11] 4,153,627

[45] May 8, 1979

[54] SULPHONIC ACIDS AND SULPHONATES

[75] Inventors: Pierre Delbende, Rouen; Jean P. Heraud, Notre-Dame de Gravenchon, both of France

[73] Assignee: Exxon Research & Engineering Co., Florham Park, N.J.

[21] Appl. No.: 768,227

[22] Filed: Feb. 14, 1977

[30] Foreign Application Priority Data

Feb. 20, 1976 [GB] United Kingdom ............ 6775/76

[51] Int. Cl.$^2$ .................................. C07C 143/24
[52] U.S. Cl. ....................................... 260/505 P
[58] Field of Search ................ 260/505 A, 505 P

[56] References Cited

U.S. PATENT DOCUMENTS 2,706,736  4/1955  Birch et al. ..................... 260/505

*Primary Examiner*—A. Siegel
*Attorney, Agent, or Firm*—Frank T. Johmann

[57] ABSTRACT

Sulphonic acids and sulphonates containing olefines and optionally water which improve color and thermal stability and also simplify purification of the acid.

20 Claims, 2 Drawing Figures

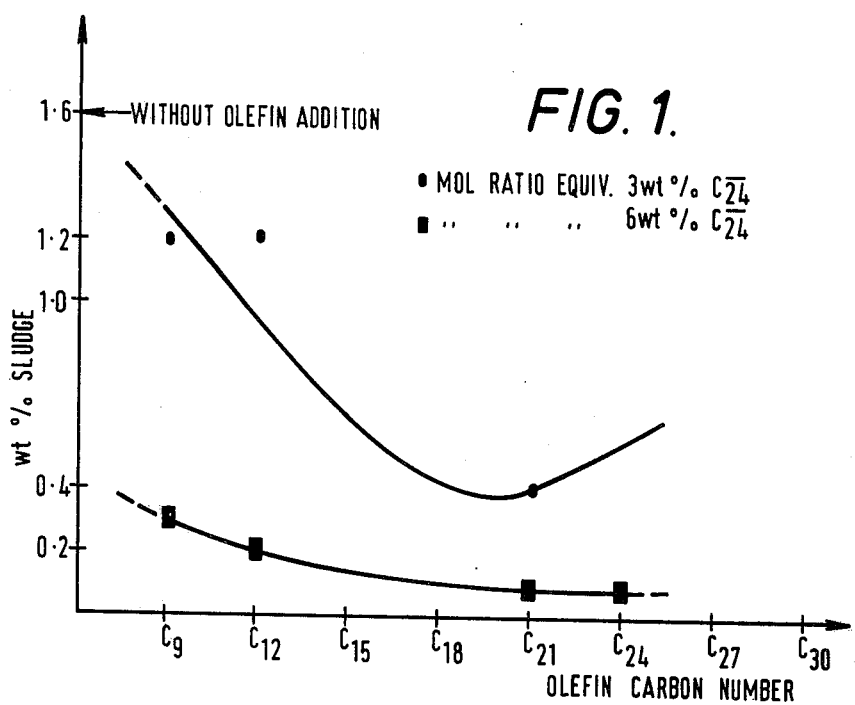
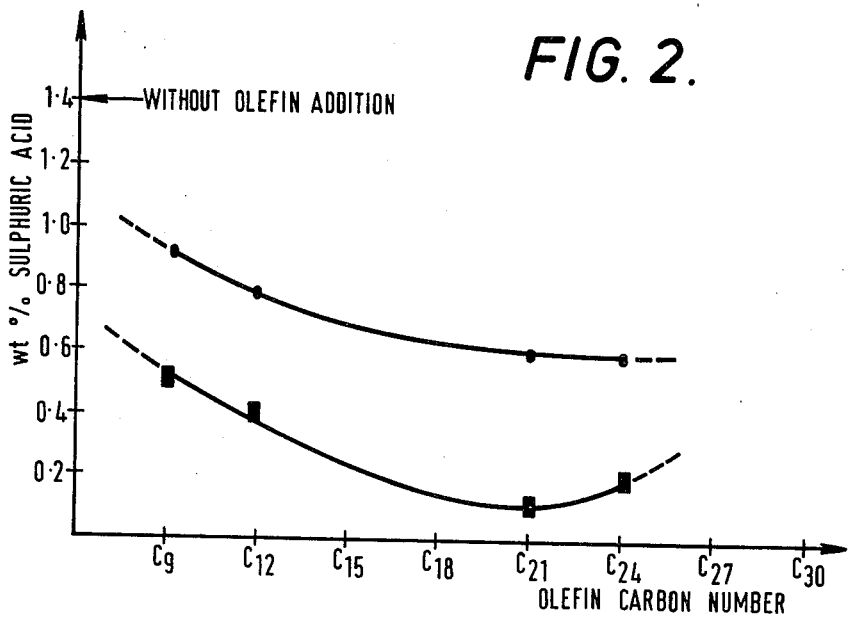

SULPHONIC ACIDS AND SULPHONATES

The present invention relates to alkylaryl sulphonic acids and sulphonates. In one aspect the invention is concerned with stabilising the sulphonic acid to inhibit the formation of undesirable coloration which appears in sulphonates upon neutralisation of sulphonic acids that have been stored. In another aspect the invention is concerned with retarding the thermal degradation of alkylaryl sulphonic acids to sulphuric acid that occurs on ageing. In one further aspect the invention is directed at simplifying the purification process that is currently needed in the production of alkylaryl sulphonic acids.

Whilst the present invention is applicable to alkylaryl sulphonic acids in general it is especially applicable to those containing comparatively long chain (i.e. 18 or more carbon atoms) alkyl groups where the problems of purification and colour and thermal stability are that much more acute.

Alkylaryl sulphonic acids are generally produced by first alkylating the chosen aryl compound with an olefin by reaction in the presence of an alkylation catalyst such as boron trifluoride or aluminium trichloride. The alkyl aryl compound is then sulphonated by reaction with sulphuric acid, with oleum, with gaseous trioxide or with a mixture of sulphur trioxide dissolved in sulphur dioxide, this latter process being preferred. The product of the sulphonation is the crude sulphonic acid mixed with the sulphonation agent and a mixture of other residues known as sludge.

In the preferred process where sulphur dioxide is present the sulphonic acid is purified by first stripping to remove the residual sulphur dioxide. The material left after this stripping is then decanted with a hydrocarbon solvent such as hexane to cool and liberate the hexane insoluble byproducts known as sludge. From about 0.5% to 1.5 wt.% of sulphuric acid is left in the sulphonic acid and this is then removed by washing with aqueous hydrochloric acid solution.

Thus, as may be seen, the process required for purifying the alkylaryl sulphonic acids in complex and therefore expensive. The purification problems vary with the length and configuration of the alkyl chain in the alkylarylsulphonic acids but despite the elaborate purification techniques described above the sulphonic acids still tend to degrade thus decreasing the sulphonic acid concentration with an increase in sulphuric acid content which is undesirable. In addition ageing of the sulphonic acids tends to result in discoloration upon neutralisation to form sulphonates at ambient temperature and particularly at the elevated temperatures sometimes required for storage and/or transportation of the sulphonates.

Various methods have been proposed for retarding the development of colour and/or the thermal degradation of alkylaryl sulphonic acids. For example U.S. Pat. No. 3,681,443 states that α-B unsaturated carboxylic acids or their anhydrides may be added to sulphonic acids. This patent is primarily concerned with alkylaryl sulphonic acids where the alkyl chain is comparatively short (around twelve carbon atoms) and we have not found these techniques effective with higher molecular weight materials. In our own Patent Application No. 5100/75 we show that the problems of colour formation in alkylaryl sulphonic acids may be reduced by incorporating an ether in the sulphonic acid.

We have now found that the problems of undesirable development of colour in sulphonic acids may be significantly reduced at ambient and elevated temperatures by incorporating an olefin in the sulphonic acid and furthermore that the purification process may not be needed if the olefin is incorporated into the crude sulphonic acid obtained from the sulphonation process. We have in addition found that the stability of the sulphonic acid is further improved, particularly the thermal stability if water is present in the sulphonic acid as well as the olefin. Addition of water to sulphonic acids is known from U.K. Pat. No. 804389 but we have found that for the desired improvement in thermal stability both olefin and water should be present. containing at least 1% by weight of an olefin based on the weight of the sulphonic acid.

In a second aspect the present invention further provides an alkylaryl sulphonic acid containing at least 1% by weight of an olefin and at least 1% by weight of water based on the weight of the sulphonic acid.

The sulphonic acids of the present invention are suitable for reaction with bases to form sulphonates thus in a further aspect the present invention provides alkylaryl sulphonates containing at least 1% by weight of an olefin based on the weight of sulphonic acid from which the sulphonate is derived.

In yet another aspect the present invention provides an alkylaryl sulphonate containing at least 1% by weight of an olefin and at least 1% of water based on the weight of the sulphonic acid from which the sulphonate is derived.

We have found that the colour stability of the alkylaryl sulphonic acid can be improved by incorporating the olefin at any stage of the sulphonation process although we prefer it be incorporated after sulphonation since incorporation before or during sulphonation tends to reduce the yield of sulphonic acid. We find that the thermal stability can be improved by incorporating the water at any stage after sulphonation providing the final sulphonic acid also contains the olefin.

Thus the present invention provides a process for improving the colour stability of an alkylaryl sulphonic acid comprising incorporating at least 1% by weight of an olefin into the sulphonic acid or during the sulphonation process, the weight of olefin being based on the weight of the resulting sulphonic acid. Within this process if it is desired to also increase the thermal stability of the sulphonic acid at least 1% by weight of water based on the weight of the sulphonic acid, may also be included any time from after sulphonation to shortly after the completion of purification. In our preferred process the olefin and the water are added together sometime after sulphonation.

We have further found that when sulphonation is effected with sulphur trioxide dissolved in sulphur dioxide the need for purifying the alkylaryl sulphonic acid so produced can be obviated if after sulphonation the sulphur dioxide is removed whilst an olefin is present. Thus, in one further aspect the present invention provides a process for stabilising an alkylaryl sulphonic acid which has been prepared by sulphonating an alkylaryl hydrocarbon with sulphur trioxide dissolved in sulphur dioxide and wherein the sulphur dioxide is removed after sulphonation characterised by removing at least part of the sulphur dioxide whilst the product of sulphonation contains at least 1% by weight of an olefin based on the weight of sulphonic acid.

Sulphonates are produced by neutralisation of the sulphonic acids and thus the present invention further provides a process for the production of sulphonates comprising neutralising sulphonic acids with base in the presence of at least 1% by weight of the sulphonic acid of an olefine.

In addition the invention provides a process for the production of sulphonate comprising neutralising sulphonic acids with base said sulphonic acid containing at least 1% of its weight of an olefin and at least 1% of its weight of water.

The techniques of our invention are generally applicable to alkylaryl sulphonic acids including acids derived from mono- or poly- nuclear aromatic compounds. The invention is however primarily concerned with sulphonic acids derived from mono-nuclear aromatic compounds; the aromatic nucleus may contain the single alkyl group as in the alkyl benzenes or two alkyl groups such as in the alkyl toluenes or three alkyl groups such as for example in the alkyl xylenes. Thus the sulphonic acid may be of the formula:

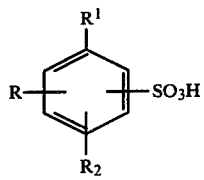

where $R^1$ and $R^2$ may be hydrogen or hydrocarbyl groups and R is an alkyl group which preferably contains from 7 to 30 carbon atoms. Although the techniques of our invention are applicable to sulphonic acid in which R is a comparatively short chain alkyl group such as from $C_7$ to $C_{15}$ they prove especially useful with the sulphonic acids in which R is longer chain such as from $C_{20}$ to $C_{30}$ which require special purification techniques. We find the techniques of our invention to be particularly suited to the production of sulphonic acids based on alkyl aryl compounds in which the alkyl group contains from 20 to 30 carbon atoms.

Any suitable olefin may be used in the technique of our invention, but we prefer to use a liquid olefin and the choice naturally is a question of economics.

The particular olefin that should be used will depend upon the nature of the sulphonic acid and the preferred olefine may be found by experimentation to determine which olefine is most effective at reduction of sludge and sulphuric acid together with improved colour stability in the particular acid. We have found, for example, that an olefine of molecular weight from 294 to 336 is most suitable for use with a $C_{24}$ alkyl benzene sulphonic acid. We prefer to use a mono-olefine since di-olefines are more expensive and although they impart some improvement to the sulphonic acid and sulphonates we find them less effective than mono-olefines.

We have found however that propylene oligomers especially trimers, tetramers and octamers are particularly suitable more so since they tend to be readily available. Since for many applications sulphonic acids are used as solutions in oil it is preferred that the olefin be oil soluble and thus olefins containing from 9 to 30 carbon atoms are especially suitable, those containing from 12 to 24 carbon atoms being most preferred. The quantity of olefin that is used depends upon the degree of stability required, the nature of the sulphonic and the time during the process in which it is added. Again for economic reasons we prefer to use as little as possible although we find at least 1% by weight should be used preferably from 2% to 10% by weight more preferably from 3% to 6% by weight. As mentioned sulphonic acids are often supplied as concentrates in an oil and in certain instances the olefin may replace part or all of the oil and in this instance more than 10% will be present.

No special blending techniques are required and the olefin may be incorporated to improve the colour stability of the sulphonic acid it may be included at any time during or immediately after the production of the sulphonic acid. However, we have found that if the olefin is present during removal of the sulphur dioxide when the alkylaryl compound has been sulphonated with a solution of sulphur trioxide in sulphur dioxide then the amount of sludge that remains after removal of the sulphur dioxide is considerably reduced as is the amount of sulphuric acid. We have found in certain instances that the reduction in sludge and sulphuric acid even in the production of sulphonic acids based on the longer chain alkylates is sufficient that it may not be necessary to remove sludge by decanting with a hydrocarbon solvent or to wash with aqueous hydrochloric acid solution to remove sulphuric acid. As can be seen this would lead to a considerable simplification of the process for manufacturing sulphonic acids. We also find that within normal operating limits the temperature at which the olefine is mixed with the sulphonic acid is not critical.

Where the olefin is added prior to or during removal of the sulphur dioxide the olefin must not of course be removed with the sulphur dioxide. Thus, in this instance the olefin should not boil under the conditions that are applied during removal of the sulphur dioxide.

As with the olefin it is not necessary to use any particular conditions to incorporate the water into the sulphonic acid. Thus when water is used it may be introduced together with the olefin or the two introduced separately. As with the olefin the amount of water that is used depends on the degree of stability required, the nature of the sulphonic acid and the time during the process in which it is added. We find however that where improved thermal stability is required at least 1% by weight of water should be used and preferably no more than 5% since more than 5% can amount to an undesirable dilution of the acid and can lead to processing and storage problems.

Sulphonic acids are generally neutralised to give sulphonates that are used as detergents where they are generally used as their salts with alkali metals, generally sodium, or with quarternay nitrogenous cations. Sulphonates with the longer alkyl chain lengths may be used as emulsifiers in the formation of oil in water emulsions as for example in lubricating oils for metal working; here again the sulphonates are usually the sodium or ammonium salts including ethoxylated ammonium salts. Sulphonic acids are also used in the production of highly basic sulphonates of the type that are used as detergent additives in lubricating oils. In this instance the sulphonates are normally highly basic calcium, magnesium or barium salts. The sulphonic acids are generally supplied as solutions in oils, which may be concentrates and the nature of the oil is not important although we prefer to use the well-known paraffinic mineral oils. The concentrates preferably contain from 50% to 95% by weight usually 65% to 90% by weight of the sulphonic acid.

The present invention is illustrated but in no way limited by referece to the following Examples some of which are by way of comparison. In these Examples the colour was determined by forming the sodium salt by neutralising a 7% active ingredient solution of the acid with an excess of a solution of 40% sodium hydroxide and heating to 130° C. to boil off the water formed. The colour of this freshly formed sodium sulphonate was then measured by the ASTM test D-1500-64 as reapproved in 1973.

The thermal stability of the sulphonic acids was determined by storing the acids at certain temperatures for certain lengths of time and measuring the decrease in sulphonic acid content over that period of time. The acid content is measured by dissolving one gram of the acid in 10 cc's of 91% isopropyl alcohol adding 90 cc's of water and 4 to 5 drops of phenol phthaline and titrating with N/10 potassium hydroxide until just pink. This solution is then acidified with N/2 hydrochloric acid until the clear colour returned. 25 cc's of a solution of the hydrochloride of paratoluidene (8 grams in 100 cc's) are then added and the mixture extracted three times with carbon tetrachloride. The remaining solution of the acid is mixed with 100 cc's of 91% isopropyl alcohol and 9 to 10 drops of meta cresol and titrated with N/10 potassium hydroxide until the solution just turns grey.

The acid index (milligrams) is $$C \times V_1 \times 56.1/1000 \times m \times 1000$$

where
- m is original weight of the acid
- C is normality of the potassium hydroxide
- $V_1$ is total original volume of potassium hydroxide the % of sulphonic acid present is:

$$C \times V_2 \times M_w/1000 \times m \times 100$$

where
- $V_2$ is volume of second charge of potassium hydroxide
- C is normality of second charge of potassium hydroxide
- $M_w$ is molecular weight of the sulphonic acid the % of sulphuric acid present is:

$$C \times (V_1 - V_2) \times 49/1000 \times m \times 100$$

In these Examples the weight of olefin is based on the total weight of acid and any diluent oil that is present.

EXAMPLE 1

The sulphonic acid of $C_{24}$ alkyl benzene was prepared by standard alkylation of benzene and then sulphonation of the alkylate with a solution of sulphur trioxide in sulphur dioxide under standard conditions. The sulphonic acid was purified by stripping to remove sulphur dioxide, decantation with hexane to remove sludge and washing with aqueous hydrochloric acid solution to remove sulphuric acid.

The sulphonic acid was diluted as necessary with a paraffinic mineral oil of viscosity about 90 S.S.U. at 100° F. to give a composition containing 90% by weight of sulphonic acid as active ingredient. This composition together with the composition to which had been added various amounts of a $C_{24}$ olefin were stored for 4 days at 120° C. and the colour of each sample measured after 4 days with the following results:

|  | Initial Color | Color after after 4 Days at 120° C |
|---|---|---|
| Acid alone | 3.0 | 4.5 |
| Acid + 1 wt.% olefin | 3.0 | 4.5 |
| Acid + 2 wt.% olefin | 3.0 | 4.5 |
| Acid + 3 wt.% olefin | 3.0 | 3.5 |
| Acid + 5 wt.% olefin | 3.0 | 3.0 |
| Acid + 10 wt.% olefin | 3.0 just under | 3.0 |
| Acid + 20 wt.% olefin | 3.0 | 3.0 |

EXAMPLE 2

The techniques of Example 1 were repeated with the exception that the sulphonic acid was diluted with the oil used in Example 1 to give a composition containing 70% by weight of sulphonic acid as active ingredient. The results were as follows:

|  | Initial Color | Color after 4 Days at 120° C |
|---|---|---|
| Acid alone | 3.0 | 7.5 |
| Acid + wt. % olefin | 3.0 | 4.0 |
| Acid + wt. % olefin | 3.0 just under | 4.0 |

EXAMPLE 3

The sulphonic acid of $C_{12}$ orthoxylene was prepared under similar conditions to those used to prepare the sulphonic acid of Example 1. This sulphonic acid is more susceptible to degradation and colour formation than that used in Example 1 as is shown by storing a 90% active ingredient composition for 6 days at 80° C. which gave the following results:

|  | Initial Color | Color after 6 Days at 80° C. |
|---|---|---|
| Acid alone | 2.5 | 3.0 |

When the acid was blended with olefin the results were as follows:

|  | Initial Color | Color after 6 Days at 80° C. |
|---|---|---|
| Acid + 1 wt.% olefin | 2.5 | 3.0 |
| Acid + 2 wt.% olefin | 2.5 | 3.0 (just under) |
| Acid + 3 wt.% olefin | 2.5 | 2.5 |
| Acid + 5 wt.% olefin | 2.5 | 2.5 |
| Acid + 10 wt.% olefin | 2.5 just under | 2.5 (just under) |
| Acid + 20 wt.% olefin | 2.5 | 2.5 (just under) |

EXAMPLE 4

Tests were carried out with the acid of Example 3 diluted to 70% active ingredient with the oil of Example 1 and storing at 100° C. for 4 days with the following results:

|  | Initial Color | Color after 4 Days at 100° C |
|---|---|---|
| Acid alone | 2.5 | 4.5 |
| Acid + 1 wt. % olefin | 2.5 | 4.0 (just under) |
| Acid + 3 wt. % olefin | 2.5 | 3.5 |
| Acid + 5 wt. % olefin | 2.5 | 3.5 (just under) |

EXAMPLE 5

The techniques of Example 2 were repeated using the diluent oil of Example 1 (A), a diluent oil of viscosity 100 S.S.U. at 100° F. (B) and also using the olefin itself as diluent.

The various formulations were stored for 4 days at 120° C. with the following results:

| | Diluent | | | Color | |
|---|---|---|---|---|---|
| | Parts A | Parts B | Parts Olefin | Initial | After 4 Days |
| 1 | 100 | — | 0 | 3.0 | 7.5 |
| 2 | 95 | — | 5 | 3.0 | 4.0 |
| 3 | 90 | — | 10 | 3.0 | 3.5 |
| 4 | 75 | — | 25 | 3.0 | 3.0 |
| 5 | 50 | — | 50 | 3.0 | 3.0 |
| 6 | 0 | — | 100 | 3.0 | 3.0 |
| 7 | — | 100 | 0 | 3.0 | 8.0 |
| 8 | — | 95 | 5 | 3.0 | 5.0 |
| 9 | — | 90 | 10 | 3.0 | 3.5 |
| 10 | — | 75 | 25 | 3.0 | 3.0 |
| 11 | — | 50 | 50 | 3.0 | 3.0 |

Formulations 1, 2, 3, 6, 7, 8 and 9 were stored for one further day at 120° C. to give the following colour readings:

| Formulation | Color |
|---|---|
| 1 | 8.0 |
| 2 | 6.5 |
| 3 | 6.0 |
| 6 | 3.0 |
| 7 | 8.0 |
| 8 | 6.5 |
| 9 | 6.0 |

Formulation 6 had a colour of 4.5 after standing for 13 days at 120° C.

EXAMPLE 6

The colour stability of the acid of Example 1 was tested using different olefins at varying concentrations an determining the colour after storage for 4 days at 120° C. The results were as follows:

| | | Color after 4 Days at 120° C. | | | |
|---|---|---|---|---|---|
| Olefin Used | Quantity of Olefin % | 0 | 1 | 3 | 5 |
| $C_9$ | | 4.5 | 4.5 | 3.0 | 2.5 |
| $C_{12}$ | | 4.5 | 4.5 | 3.0 | 3.0 |
| $C_{24}$ | | 4.5 | 4.5 | 3.0 | 3.0 |
| $C_{30}$ | | 4.5 | 4.5 | 3.5 | 3.0 |

EXAMPLE 7

The acid prepared according to the process of Example 1 was analysed for sludge content and sulphuric acid content immediately after removal of the sulphur dioxide. It was found to contain 1.5 wt.% of sludge (i.e. the portion insoluble in hexane) and 1.5 wt.% of sulphuric acid and washing with aqueous hydrochloric acid solution was necessary to obtain an acceptable produce (low sulphuric acid content).

Similar analyses were made on products in which certain amounts of the $C_{24}$ olefin used in Example 1 were added to the sulphonation product prior to removal of the sulphur dioxide. The amounts of olefin quoted are based on the starting amount of the $C_{24}$ alkyl benzene.

| | Amount of Olefin | | |
|---|---|---|---|
| | 3.5% | 5% | 7% |
| Sludge wt. % | 0.1 | 0.0 | 0.0 |
| $H_2SO_4$ wt. % | 0.9 | 0.3 | 0.9 |
| Initial Color of | 3.5 | 2.5 | 1.5 |

| | Amount of Olefin | | |
|---|---|---|---|
| | 3.5% | 5% | 7% |
| Sulphonic Acid | | | |

There was no washing with aqueous hydrochloric acid solution in the preparation of these acids.

EXAMPLE 8

The techniques of Example 7 were repeated except that the acid that was tested was diluted to 70 wt.% active ingredient. The sludge, sulphuric acid and colour levels were all substantially the same as in Example 7.

EXAMPLE 9

The thermal stability of the acid of Example 2 was determined using various diluents by measuring the sulphonic acid content of the various solutions after storage for 4 days at 120° C.

| Diluent | Initial Sulphonic Acid Content % | Sulphonic Acid Content After 4 Days at 120° C. |
|---|---|---|
| 100 Parts A | 69.0 | 67.8% |
| 100 Parts B | 68.8 | 67.8% |
| 100 Parts Olefin | 68.8 | 67.8% |
| 50 Parts A | 69.3 | 68.2% |
| 50 Parts Olefin | | |

EXAMPLE 10

The thermal stability of the sulphonic acid of Example 1 diluted to 70% active ingredient with the paraffinic mineral oil of Example 1 and with the $C_{24}$ olefin used in Example 1 were determined by measuring the sulphonic acid content of the solutions after various storage periods at certain temperatures. The results were as follows:

| Original Acid Content | Content After 5 Days at 120° C. | Content After 6 Months at 60° C |
|---|---|---|
| 88.5% | 84.7% | 86.0% |
| 69.0% | 67.7% | 67.5% |
| (in oil of Example 1) | | |
| 69.0% | 67.7% | 67.5% |
| (in $C_{24}$ olefin) | | |

EXAMPLE 11

The acid of Example 1 (90% active ingredient) was blended with varying amounts of $C_{24}$ olefin and water and the thermal stability of the acid determined by measuring the sulphonic acid content after storage with the following results:

| | Initial % Sulphonic Acid | After 6 Weeks at 80° C. | After 5 Days at 120° C. |
|---|---|---|---|
| Acid alone | 86.5 | 84.9 | 84.7 |
| Acid + 2 wt.% olefin | 85 | 83.3 | 83.0 |
| Acid + 2 wt.% olefin + 2 wt.% water | 83.0 | 82.5 | 81.7 |
| Acid + 2 wt.% olefin + 4 wt.% water | 81.5 | 81.5 | 81.0 |

EXAMPLE 12

The tests of Example 11 were repeated using the 70% active ingredient acid of Example 2 with the following results:

|  | Initial % Sulphonic Acid | After 6 Weeks at 80° C. | After 5 Days at 120° C. |
|---|---|---|---|
| Acid alone | 69.0 | 68.5 | 67.7 |
| Acid + 2 wt.% olefin | 67.7 | 67.2 | 66.6 |
| + 2 wt.% olefin + 2 wt.% water | 66.6 | 66.6 | 66.4 |
| Acid + 2 wt.% olefin + 4 wt.% water | 65.2 | 65.2 | 65.2 |

EXAMPLE 13

The effect of the addition of water on the colour stability of the sulphonic acid of Example 1 was assessed with the following results:

| Olefin wt. % added | 0.0 | 0.0 | 1.0 | 1.0 | 2.0 | 2.0 | 2.0 |
|---|---|---|---|---|---|---|---|
| Water wt. % added | 0.0 | 5.0 | 0.0 | 5.0 | 0.0 | 2.0 | 4.0 |
| Initial Color | 3 | 2.5 | 3 | 2.5 | 3 | 2.5 | 2.5 |
| Color after 3 Days at 120° C. | 4 | 4 | 4 | 4 | 3 | 3 | 2.5 |
| Color after 5 days at 120° C. | 6 | 6 | 6 | 6 | 3.5 | 4 | 4 |

This shows that the addition of water does not remove the colour benefits of adding the olefine The addition of up to 4% of water alone was found to have virtually no effect on the thermal stability of the sulphonic acid.

EXAMPLE 14

The effect of the addition of water on the colour stability of the sulphonic acid of Example 2 was assessed with the following results:

| Olefin wt. % added | 0.0 | 2.0 | 2.0 | 2.0 |
|---|---|---|---|---|
| Water wt. % added | 0.0 | 0.0 | 2.0 | 4.0 |
| Initial Color | 3.5 | 3 | 3 | 2.5 |
| Color after 3 Days at 120° C. | 6.5 | 3 | 3 | 3 |
| Color after 5 Days at 120° C. | 8.0 | 3.5 | 4.5 | 4 |

The addition of up to 5% water to the acids of Example 1 and Example 2 was found to have substantially no effect on product viscosity.

EXAMPLE 15

The effect of the molecular weight of the olefine on the development of sludge and sulphuric acid was assessed by adding different olefines to the freshly formed sulphonic acid of Example 1. 2 series of experiment were carried out, in the first the amount of olefine used was such as to give a mole amount of the olefine equivalent to using 3 wt.% of the $C_{24}$ olefine based on the weight of $C_{24}$ alkyl benzene used in the production of the sulphonic acid. In the second series the amount of olefine used corresponded to 6 wt.% of the $C_{24}$ olefine based on the weight of the $C_{24}$ alkyl benzene used in the production of the sulphonic acid.

The $C_9$ and $C_{12}$ olefines were commercially available materials sold as $C_9$ and $C_{12}$ average cuts whilst the $C_{15}$ and $C_{27}$ average materials were narrow cuts obtained from distillation of a $C_{24}$ average olefine.

The sludge content of the acids of the two series of experiments is shown in the graph of FIG. 1 of the accompanying drawings as the weight percent of sludge based on the weight of the alkyl benzene used in the production of the sulphonic acid.

The sulphuric acid content of the acids of the two series of experiments is shown in the graph of FIG. 2 of the accompanying drawings as the weight percent of sulphuric acid based on the weight of the sulphonic acid.

EXAMPLE 16

For the sake of comparison maleic anhydride and a $C_{24}$ olefine were added to a 90% active ingredient and a 70% active ingredient $C_{24}$ alkyl benzene sulphonic acid prepared substantially according to Example 1 and the colour stability measured by determining the difference in colour rating of sulphonate formed upon neutralisation of the freshly formed acid and that formed by neutralisation after storage for 4 days at 120° C. with the following results

|  | No Additive | 2 wt % Maleic Anhydride | 2 wt % $C_{24}$ olefine |
|---|---|---|---|
| 90% active ingredient | 2 | 2 | 0.5 |
| 70% active ingredient | 4 | 4 | 1 |

Thus showing that the presence of maleic anhydride had substantially no effect on colour stability.

EXAMPLE 17

For the sake of comparison the techniques of Example 7 in which the olefine is added prior to removal of sulphur dioxide and there is no washing with aqueous hydrochloric acid was repeated using maleic anhydride as the additive. The difference in the colour rating of the sulphonate by immediate neutralisation of the acid and neutralisation after standing for 4 days at 120° C. were as follows:

|  | No Additives | 2 wt % Maleic Anhydride | 4 wt % Maleic Anhydride |
|---|---|---|---|
| Color Change | 2 | 3 | 3 |

Hereagain showing that the presence of the maleic anhydride does not improve but if anything worsens colour formation.

EXAMPLE 18

Also for comparison the techniques of Example 7 were repeated with the addition of maleic anhydride immediately after sulphonation and measuring the sludge and sulphuric acid content of the sulphonic acid. This was compared with a similar technique in which the $C_{24}$ olefine was used and the results were as follows:

|  | No Additive | 2 wt % Maleic Anhydride | 4 wt % Maleic Anhydride | 3 wt % $C_{24}$ Olefine |
|---|---|---|---|---|
| Sludge | 1.3 | 3.0 | 3.7 | 0.2 |
| Sulphuric Acid | 1.2 | 1.8 | 1.8 | 0.4 |

We claim:

1. A process for improving the colour stability of an alkylaryl sulphonic acid comprising incorporating at least 1% up to about 10% by weight of an olefin having about 9 to 30 carbon atoms into the sulphonic acid or during the sulphonation process of producing said sulphonic acid wherein an alkylaryl compound is sulphonated by reaction with a sulphonating agent selected from the group consisting of sulphuric acid, oleum, gaseous sulphur trioxide, and a mixture of sulphur trioxide dissolved in sulphur dioxide followed by stripping to remove sulphur dioxide; the weight of the olefine being based on the weight of the resulting sulphonic acid, and wherein when said olefin is incorporated during the sulphonation process utilizing said mixture of sulphur trioxide dissolved in sulphur dioxide, said olefin is added before complete removal of sulphur dioxide by stripping and said olefin is not removed with the stripping of the sulphur dioxide.

2. A process according to claim 1 in which at least 1% by weight of water based on the weight of the sulphonic acid is incorporated into the sulphonic acid.

3. A process according to claim 1 in which from 2% to 10% by weight of the olefine is incorporated.

4. A process according to claim 2 in which from 1% to 5% by weight of water is incorporated.

5. A process according to claim 1 in which the olefine is incorporated in the sulphonic acid immediately after the production of the sulphonic acid by sulphonation and prior to purification thereof.

6. A process according to claim 5 in which at least 1% by weight of water based on the weight of the sulphonic acid is incorporated together with the olefine.

7. A process according to claim 1 in which the sulphonic acid is of the general formula

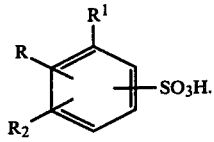

where $R^1$ and $R^2$ are hydrogen or hydrocarbyl groups and R is an alkyl group containing from 7 to 30 carbon atoms.

8. A process according to claim 1 in which the olefine contains from 12 to 24 carbon atoms.

9. A process according to claim 1, wherein said sulfonic acid has been prepared by sulfonating an alkylaryl hydrocarbon with sulfur trioxide dissolved in sulfur dioxide, and wherein said olefin has been added during the sulfonation process before the complete removal of sulfur dioxide.

10. A process according to claim 1, wherein said acid, after the addition of said olefin, is neutralized with a base.

11. A process according to claim 10, wherein said base is sodium hydroxide.

12. The product produced according to the process of claim 1.

13. The product produced according to the process of claim 2.

14. The product produced according to the process of claim 7.

15. The product produced according to the process of claim 7, wherein R contains about 20 to 30 carbon atoms.

16. The product produced according to the process of claim 8.

17. The product produced according to the process of claim 7, wherein $R^1$ and $R^2$ are hydrogen and R is an alkyl group containing 24 carbon atoms and said olefin has a molecular weight from 294 to 336.

18. The product produced according to the process of claim 9.

19. The product produced according to the process of claim 10.

20. The product produced according to the process of claim 11.

* * * * *